United States Patent
Miljanic et al.

(10) Patent No.: US 10,138,192 B2
(45) Date of Patent: Nov. 27, 2018

(54) CYCLOBENZOINS

(71) Applicant: University of Houston System, Houston, TX (US)

(72) Inventors: Ognjen Miljanic, Houston, TX (US); Qing Ji, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 15/559,817

(22) PCT Filed: Mar. 17, 2016

(86) PCT No.: PCT/US2016/022799
§ 371 (c)(1),
(2) Date: Sep. 19, 2017

(87) PCT Pub. No.: WO2016/153905
PCT Pub. Date: Sep. 29, 2016

(65) Prior Publication Data
US 2018/0050974 A1 Feb. 22, 2018

Related U.S. Application Data

(60) Provisional application No. 62/135,931, filed on Mar. 20, 2015.

(51) Int. Cl.
C07C 45/45 (2006.01)
C07C 15/00 (2006.01)
C07C 45/44 (2006.01)
C07C 49/727 (2006.01)
C07C 15/50 (2006.01)
C07C 47/544 (2006.01)
C07C 49/215 (2006.01)
C07C 49/245 (2006.01)

(52) U.S. Cl.
CPC .............. *C07C 45/45* (2013.01); *C07C 15/50* (2013.01); *C07C 45/44* (2013.01); *C07C 47/544* (2013.01); *C07C 49/215* (2013.01); *C07C 49/245* (2013.01); *C07C 49/727* (2013.01); *C07C 2601/06* (2017.05); *C07C 2603/38* (2017.05)

(58) Field of Classification Search
CPC ........ C07C 45/45; C07C 15/15; C07C 47/544
See application file for complete search history.

(56) References Cited

U.S. PATENT DOCUMENTS 4,310,699 A  1/1982 Rabilloud et al.

OTHER PUBLICATIONS

International Patent Application No. PCT/US2016/022799 International Search Report and Written Opinion dated Jun. 9, 2016 (14 pages).
Pinaud et al., "Step-Growth Polymerization of Terephthaldehyde Catalyzed by N-Heterocyclic Carbenes," Macromolecules, Jun. 24, 2009, vol. 42, p. 4932-4936.
Zhao et al., "Facile Approach to Preparing Microporous Organic Polymers through Benzoin Condensation," Applied Materials & Interfaces, Nov. 30, 2012, vol. 4, p. 6975-6981.
Kratzer et al., "Modified benzoin condensation of terephthalaldehyde with benzaldehyde," Journal of Organic Chemistry, Jun. 1976, vol. 41, p. 2230.
Jones et al., "The benzoin reaction with terephthalaldehyde," Journal of the Chemical Society, 1955, p. 1286-1287.

*Primary Examiner* — Sikarl A Witherspoon
(74) *Attorney, Agent, or Firm* — Conley Rose, P.C.

(57) ABSTRACT

One-step cyanide-catalyzed benzoin condensations for synthesizing shape persistent cyclobenzoin macrocycles. Selected dialdehydes, and cyanide salts are reacted in aqueous solvents to form such cyclobenzoin macrocycles.

21 Claims, 9 Drawing Sheets

CYCLOBENZOINS

CROSS-REFERENCE TO RELATED APPLICATIONS

This application is a 35 U.S.C. § 371 national stage entry of PCT/US2016/022799, filed Mar. 17, 2016, which claims priority to U.S. Provisional Application No. 62/135,931, filed on Mar. 20, 2015, each of which is herein incorporated in its entirety by reference.

STATEMENT REGARDING SPONSORED RESEARCH

The invention described and claimed herein was made in part utilizing funds supplied by Welch Foundation Grant E-1768 and National Science Foundation Grant CHE-1151292.

BACKGROUND

Field of Disclosure

This disclosure generally relates to the one-step synthesis, and composition of a new class of macrocyclic molecules called cyclobenzoins. More particularly this disclosure is drawn to methods of preparing cyclobenzoins from aromatic dialdehydes (including but not limited to isophthaldehyde, terephthaldehyde, and phthaldehyde) and larger versions thereof in a single step through a catalyzed benzoin condensation. Most particularly, this disclosure is drawn to a method of making cyclotribenzoin and cyclotetrabenzoin.

Background of the Technology

The chemistry of macrocycles spans the fields of organic, inorganic, and supramolecular chemistry. Macrocycles play a developmental role in areas including, but not limited to: aromaticity, porous materials, and supramolecular binding. However, macrocyclic molecules are synthetically challenging because macrocyclization reactions are entropically unfavorable, and as such, the prior art is often restricted to long and indirect synthetic routes of such molecules. Additionally, macrocycles that are obtained from nature or that can be readily synthesized (such as cyclodextrins or cucurbiturils) present further challenges in terms of selective derivatization.

BRIEF SUMMARY OF THE DISCLOSED EMBODIMENTS

In contrast, disclosed herein is a one-step synthesis of benzoin-based macrocycles, which in some embodiments may be selectively derivatized. In other embodiments, such macrocycles may be ornamented with multiple oxygen-based functional groups (see Ji, Q., Le, H. T. M., Wang, X., Chen, Y.-S., Makarenko, T., Jacobson, A. J. and Miljanić, O. Š. (2015), Cyclotetrabenzoin: Facile Synthesis of a Shape-Persistent Molecular Square and Its Assembly into Hydrogen-Bonded Nanotubes. Chem. Eur. J., 21: 17205-17209. doi:10.1002/chem.201503851; and Ji, Q., Do L. H.; and Miljanić, O. Š. (2015), Cyclotribenzoin. Synlett; 26(11): 1625-1627; incorporated herein in their entirety by reference).

In order to address unfulfilled needs, the disclosure provides in some embodiments described herein: embodiments of a one-step method of synthesizing a cyclobenzoin macrocycle, wherein the method comprises reacting a dialdehyde, and a cyanide salt in an aqueous solvent mixture to form a cyclobenzoin macrocycle, wherein the solvent is an alcohol, and wherein in some embodiments, the alcohol is selected from the group consisting of 2-methoxyethanol; ethanol; methanol; propanol, butanol, and pentanol isomers, and various glycols. In some further embodiments, the solvent is in a 1:1 molar ratio with $H_2O$.

In other embodiments, the dialdehyde is selected from the group comprising isophthaldehyde; tetraphthaldehyde; phthaldehyde, and aromatic analogs thereof, wherein one or more substituted or unsubstituted aromatic or hetoroaromatic rings, and/or triple bonds are inserted between the two formyl groups. In a further embodiment, the dialdehyde is at a concentration of between 0.1M to 1M. In some embodiments, the dialdehyde is isophthaldehyde, and in further embodiments isophthaldehyde is in a concentration of about 0.5M. In some other embodiments, the dialdehyde is tetraphthaldehyde, and in some further embodiments tetraphthaldehyde in a concentration of about 0.17M. In some embodiments of the method of synthesizing a cyclobenzoin macrocycle, reacting the dialdehyde and a cyanide salt comprises heating the mixture at reflux under nitrogen gas at a temperature of about 100° C. for about 48 hrs. In a further embodiment, the reaction catalyst is selected from the group consisting NaCN and cyanide salts of metals, or organic catalysts for benzoin condensation, such as but not limited to thiazolium salts.

In some embodiments of the method of synthesizing a cyclobenzoin macrocycle, the macrocycle is cyclotribenzoin. In some other embodiments of the method of synthesizing a cyclobenzoin macrocycle, the macrocycle is cyclotetrabenzoin. In some embodiments, cyclotetrabenzoin comprises a Langmuir surface area of about 52 $m^2g^{-1}$. In some embodiments, the cyclobenzoin macrocycle forms a microporous three-dimensional organic framework, and in other embodiments, the cyclobenzoin macrocycle forms one-dimensional nanotube channel. In further embodiments, the cyclobenzoin macrocycle is porous. In some embodiments of the method of synthesizing a cyclobenzoin macrocycle, the cyclobenzoin macrocycle comprises selective derivatization and in other embodiments, the cyclobenzoin macrocycles further comprise porous materials, assemblies at liquid-solid interfaces, and organic nanowires and nanofibrils. In some embodiments, a cyclobenzoin macromolecule is disclosed wherein the cyclobenzoin comprises a synthetic receptor macromolecule. In another embodiment, the receptor macromolecule is selectively derivatized.

In some embodiments, a cyclotetrabenzoin macrocycle is disclosed which comprises a square shape-persistent 3-dimensional structure, wherein the 3-dimensional structure comprises four outer polar α-hydroxyketone moieties, and a central nonpolar cavity. In other embodiments of the cyclotetrabenzoin macrocycle, the macrocycle is intrinsically porous, and in other embodiments it comprises a 10% void volume. In further embodiments, the central non-polar cavity comprises an area of about 6.9×6.9 Å. In some embodiments, a cyclotribenzoin macrocycle is disclosed which comprises α-hydroxyketone moieties which hydrogen bond to further units of cyclotetrabenzoin forming hydrogen-bonded nanotubular subunits. In other embodiment, the α-hydroxyketone moieties comprise hydrogen bonds to molecular guest molecules, and in further embodiments of the cyclotetrabenzoin macrocycle, the α-hydroxyketone moieties are selectively derivatized. In some embodiments, a cyclotribenzoin macrocycle is disclosed which comprises a cone shape-persistent 3-dimensional structure, wherein the 3-dimensional structure further comprises convergent anionic and cationic binding groups. In further embodiments, the anionic and cationic binding groups are further derivatized, and in still further embodiments, the anionic and cationic binding groups bond with guest molecules.

BRIEF DESCRIPTION OF THE DRAWINGS

FIGS. 6A and 6B: shows the crystal packing of cyclotetrabenzoin (2'), wherein: (FIG. 6A) shows two parallel columns of (2') which forms an infinite tape of hydrogen bonds, highlighted in green (central apex), wherein the molecules on the left (first 3 rows of molecular overlays) are colored by element, those on the right (next 5 rows of molecular overlays) are colored to highlight separate nanotubes; (FIG. 6B) shows a segment of the extended crystal structure of (2'), viewed along the crystallographic c axis. This view of the structure shows the arrays of hydrogen bonded nanotubes, and the intrinsic pores of (2') in accordance with an embodiment of a method described herein;

DETAILED DESCRIPTION OF THE DISCLOSED EXEMPLARY EMBODIMENTS

It should be understood that although an illustrative implementation of one or more embodiments are provided below, the disclosed systems and/or methods may be implemented using any number of techniques, whether currently known or in existence. The disclosure should in no way be limited to the illustrative implementations, drawings, and techniques below, including the exemplary designs and implementations illustrated and described herein, but may be modified within the scope of the appended claims along with their full scope of equivalents.

The following discussion is directed to various exemplary embodiments of the invention. However, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and that the scope of this disclosure, including the claims, is not limited to that embodiment.

In the following discussion and in the claims, the terms "including" and "comprising" are used in an open-ended fashion, and thus should be interpreted to mean "including, but not limited to . . . ." As used herein, the term "about," when used in conjunction with a percentage or other numerical amount, means plus or minus 10% of that percentage or other numerical amount. For example, the term "about 80%," would encompass 80% plus or minus 8%.

Figure 1:
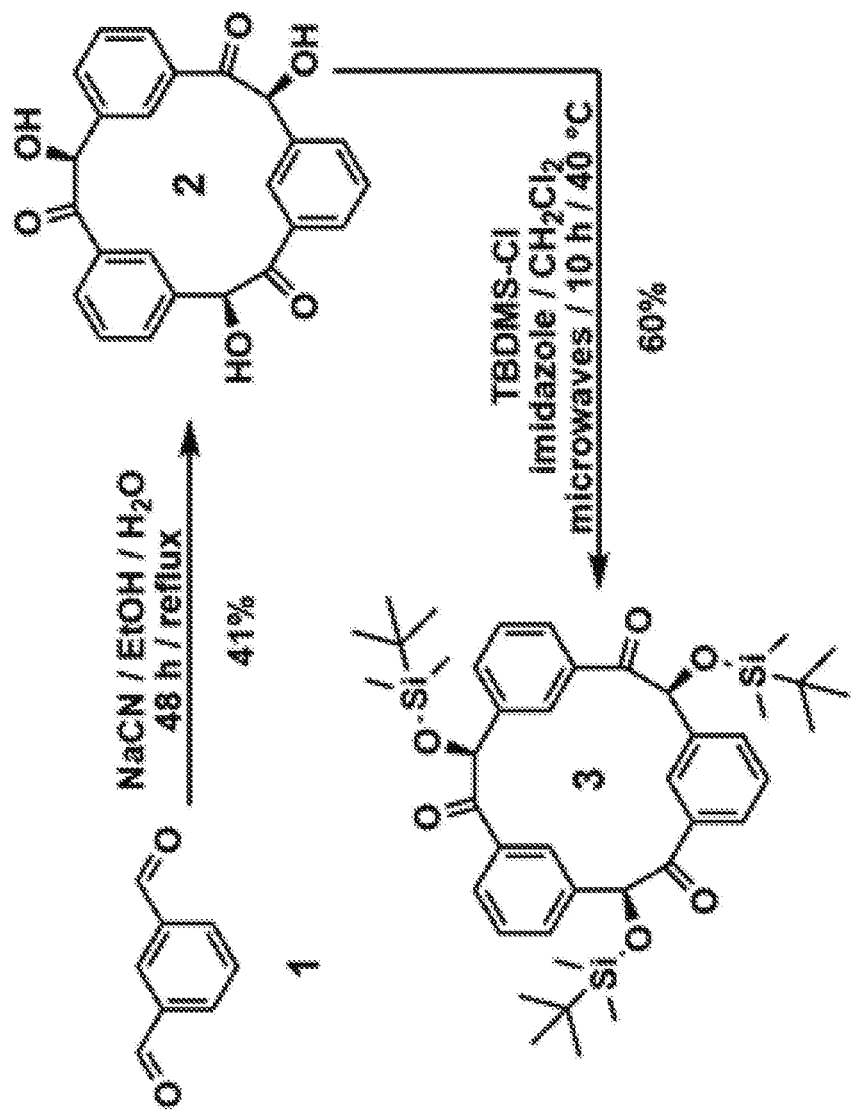
FIG. 1: shows a scheme which depicts the synthesis of cyclotribenzoin (2), and its silylated derivative (3), wherein both (2) and (3) comprise enantiomers, in accordance with an embodiment of a method described herein.

Cyanide-assisted benzoin condensation of isophthaldehyde, (wherein two molecules of aldehyde add together in the presence of a nucleophile (typically $CN^-$), to form a single bond between their former carbonyl carbon atoms) is disclosed herein as an embodiment of a method of preparing cyclotribenzoin (compound (2), FIG. 1): a cone-shaped macrocycle whose three benzene rings define a cup-like cavity, wherein six of its C—H bonds convergently point in the opposite direction. In some embodiments, the combination of convergently oriented cation and anion binding groups that populate the macrocycle and the one step synthesis makes cyclotribenzoin a suitable platform for supramolecular chemical methodologies. This macrocycle assembles into a microporous crystal structure through the formation of hydrogen-bonded nanotubes that protrude through the crystal. However, the first attempts to extend benzoin condensation to more complex precursors are disclosed herein.

Similarly, in another embodiment, cyanide-catalyzed benzoin condensation of tetraphthaldehyde produces a cyclic tetramer, termed "cyclotetrabenzoin". Cyclotetrabenzoin (compound (2'), FIG. 4) is a square shape-persistent macrocycle ornamented with four α-hydroxyketone functionalities again, pointing away from the central cavity, whose dimensions are 6.9×6.9 Å.

In some embodiments, in the solid state such functional groups extensively hydrogen bond, resulting in a microporous three-dimensional organic framework with one-dimensional nanotube channels. Cyclotetrabenzoin exhibits in some embodiments permanent porosity; in some further embodiments the porosity is low, with a Langmuir surface area of about 52 $m^2g^{-1}$. Cyclotetrabenzoin's one-step synthesis and purification provide a platform for a cost effective synthesis of further shape-persistent macrocycles, and porous molecular crystals (which in some embodiments may be selectively derivatized) via benzoin condensation. In some embodiments, such shape-persistent macrocycles and cages may be used as components of ordered three-dimensional (porous materials), two-dimensional (assemblies at liquid-solid interfaces), and one-dimensional (organic nanowires and nanofibrils) functional ensembles. These shape persistent macrocycles may further be used in specifically designed host/guest systems, and be used as synthetic receptors, wherein the macrocycles are derivatized accordingly.

SPECIFIC EXAMPLES

Example 1

Synthesis of Cyclotribenzoin and its Silylated Derivative

Disclosed herein is the reaction of isophthaldehyde ((1), FIG. 1) with NaCN, wherein the outcome of the reaction depends on the solvent and concentration of (1), wherein heating (1) with NaCN at reflux in 1:1 mixtures of $H_2O$ with either MeOH, EtOH, or t-BuOH results in the formation of trimer (2). In one embodiment, the trimer precipitated from solution when the starting concentration of (1) was 0.5M. In further embodiments when higher concentrations of (1) were used, mixtures of (2) with other noncyclic oligomers and insoluble polymers were obtained.

In other embodiments, similar results were observed if the reaction mixtures were not heated. In some embodiments, alcoholic solvents may be required for the reaction to proceed, because in a further embodiment, switching to 1,4-dioxane/$H_2O$ solvent combination completely suppressed the reaction, and the use of ethylene glycol as a solvent led to the formation of mixtures.

In one other embodiment, performing the reaction with EtOH/$H_2O$ produced (2) in 41% yield after recrystallization from 2-methoxyethanol. The yield of 41% is achieved by a one-step synthesis, and at a low cost due to the use of the inexpensive isophthaldehyde. Therefore (2) can be prepared on a cost effective multigram scale. Compound (2) cyclotribenzoin, is a white powder, soluble in DMSO, 2-methoxyethanol, THF, 1,4-dioxane, nitrobenzene, and DMF. It is insoluble in $H_2O$, acetone, MeCN, EtOAc, MeOH, EtOH, $Et_2O$, as well as in hydrocarbon and chlorinated hydrocarbon solvents.

Experimental Information for the Synthesis of Cyclotribenzoin (2):

Isophthaldehyde (1, 684 mg, 5.10 mmol), EtOH (5 mL), and deionized $H_2O$ (5 mL) were added to a round bottom flask equipped with a stirring bar, and the mixture was heated at reflux under nitrogen until all of 1 dissolved. At that time, NaCN (25 mg, 0.51 mmol) was added into the round bottom flask, and continued heating for 48 h. The precipitate obtained was filtered and then washed with deionized $H_2O$ (10 mL), EtOH (10 mL), and $Et_2O$ (10 mL). After recrystallization from 2-methoxyethanol, pure (2) was obtained (280 mg, 41%) as a white solid. Mp=245° C. (decomposition). UV/Vis (THF): $\lambda_{max}$ (log ε)=248 (4.29), 288 (3.46) nm. IR (neat): 3456 (w, ũO—H), 3070 (w, ũC—H), 2925 (ũC—H), 1682 (s, ũC=O), 1583 (s), 1432 (s), 1395 (s), 1274 (m), 1182 (m), 1083 (m), 796 (s), 743 (s), 692 (s) cm$^{-1}$. $^1$H NMR (DMSO-$d_6$, 400 MHz): δ 8.78 (s, 3H), 7.63 (d, 3JH-H=7.8 Hz, 3H), 7.45 (d, 3JH-H=7.8 Hz, 3H), 7.35 (dd, 3JH-H=7.8 and 7.3 Hz, 3H), 6.42 (d, 3JH-H=5.5 Hz, 3H), 6.01 (d, 3JH-H=5.5 Hz, 3H) ppm. $^{13}$C NMR (DMSO-$d_6$, 100 MHz): δ 198.4, 140.8, 134.9, 132.4, 130.2, 130.0, 128.2, 74.7 ppm. LRMS (ESI/[M-H]−): calcd for $C_{24}H_{18}O_6$ 401.11, found 401.13. Single crystals of (2) were obtained over 7d by vapor diffusion of $CHCl_3$ into its solution in THF (0.5 mg mL$^{-1}$).

In some embodiments, to increase the solubility of (2) in common organic solvents, (2) was converted into a t-butyldimethylsilyl (TBDMS) derivative ((3) FIG. 1), by treatment with TBDMS-Cl in $CH_2Cl_2$. (3) is significantly more soluble in most organic solvents. This increased solubility, in some embodiments, allowed probing conformational flexibility using variable-temperature NMR spectroscopy, wherein upon cooling to −85° C. in $CD_2Cl_2$, no decoalescence of peaks was observed. Some shifting of peak positions was observed, which in some embodiments may indicate aggregation or changes in intermolecular hydrogen bonding configurations.

Synthesis of macrocycle (3) occurs when compound (2) (128 mg, 0.32 mmol), imidazole (1.30 g, 19.1 mmol), and dry $CH_2Cl_2$ (15 mL) were added to a thick-walled 20 mL microwave vial. The mixture was stirred under nitrogen for 10 min. The reagent t-butyldimethylsilyl chloride (2.90 g, 19.1 mmol) was then added to the mixture. The vial was sealed, and then placed into a Biotage microwave reactor, where it was heated for 10 h at 40° C. The reaction mixture was diluted with $CHCl_3$ (50 mL), washed with $H_2O$ (50 mL), and the organic layer was separated and dried over anhydrous $MgSO_4$. After removal of solvent, the crude product was isolated as light yellow oil. Pure compound (3) was obtained after recrystallization from pentane at −78° C. (142 mg, 60%). Mp=167° C. UV-Vis (THF): $\lambda_{max}$ (log ε)=286 (3.61), 326 (3.18) nm. IR (neat): 3070 (w, ũC—H), 2929 (w, ũC—H), 1713 (s, ũC=O), 1674 (s), 1581 (s), 1471 (s), 1362 (s), 1257 (m), 1120 (m), 1028 (m), 862 (m), 781 (s), 735 (s), 698 (s) cm$^{-1}$. $^1$H NMR (CDCl$_3$, 500 MHz): δ 7.88 (s, 3H), 7.72 (d, 3JH-H=8.0 Hz, 3H), 7.73 (d, 3JH-H=7.6 Hz, 3H), 7.33 (dd, 3JH-H=8.0 and 7.4 Hz, 3H), 5.82 (s, 3H), 0.87 (s, 27H), 0.09 (s, 9H), 0.08 (s, 9H). $^{13}$C NMR (CDCl3, 125 MHz): δ 198.3, 139.2, 135.7, 131.6, 129.5, 128.9, 127.0, 79.4, 25.9, 18.5, −4.6, −4.7. LRMS (ESI/[M+Na+]): calcd for $C_{42}H_{60}O_6Si_3$ 767.36, found 767.38, and (ESI/[2M+Na+]): calcd 1511.73, found 1511.09.

X-Ray Crystal Structure

In further embodiments, diffraction-quality single crystals of macrocycle (2) were grown by vapor diffusion of $CHCl_3$ into solution in THF. (2) crystallized in the R3 space group, with three molecules of (2) and three molecules of THF per unit cell. The THF molecules are disordered over three orientations (removed from x-ray crystallography images).

Figure 2:
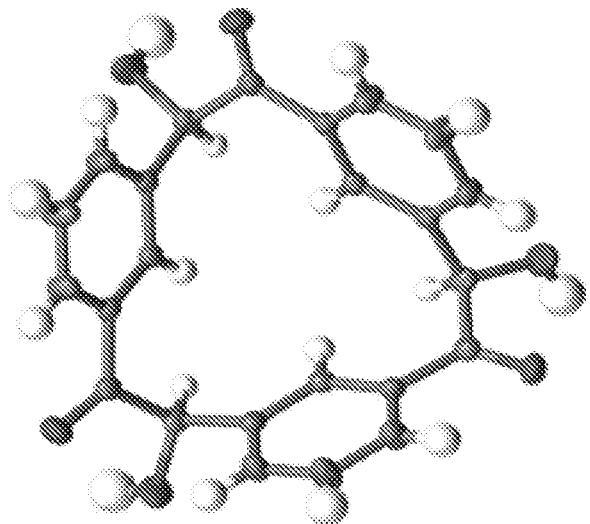
FIG. 2: shows an X-ray crystal structure of cyclotribenzoin (2). On the left, a side view shows convergent positioning of six C—H bonds in a conical structure. On the right, a top-down view of the macrocycle, and thermal ellipsoids are shown at 50% probability, in accordance with an embodiment of a method described herein.
Figure 2:
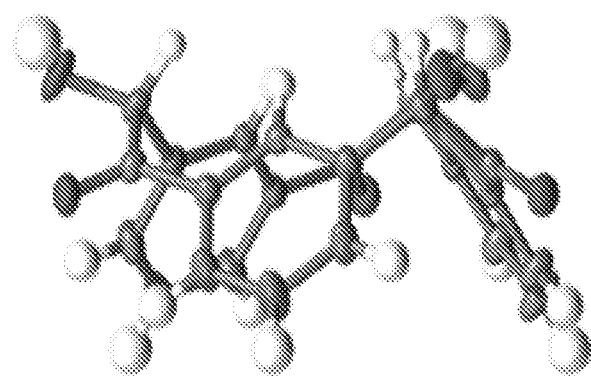

In some embodiments, the crystal structure, of cyclotribenzoin (2) is shown to comprise several structural features: such as, all three stereo-centers have the same orientation (S, in FIGS. 2), and (2) crystallizes as a racemic twin, wherein the minor component has an occupancy of ~32%, which in some embodiments indicates that enantiomers are present; (2) adopts a conical shape, where three aromatic rings define a cup-like cavity, orienting the six oxygen-based functionalities (three C=O and three O—H groups) away from it. In some embodiments, the conical shape may relieve all of the potential strain in the molecule, as all carbon atoms in (2) have bonding angles within ±2° of their idealized geometries. Further, in some embodiments, six C—H bonds—three coming from the arene rings, and three from the C—H groups in the immediate neighborhood of the hydroxy groups—point to a single spot. In other embodiments, the convergent positioning indicates that (2) and its derivatives may be used as receptors for anions based on [C—H . . . anion] interactions.

Figure 3:
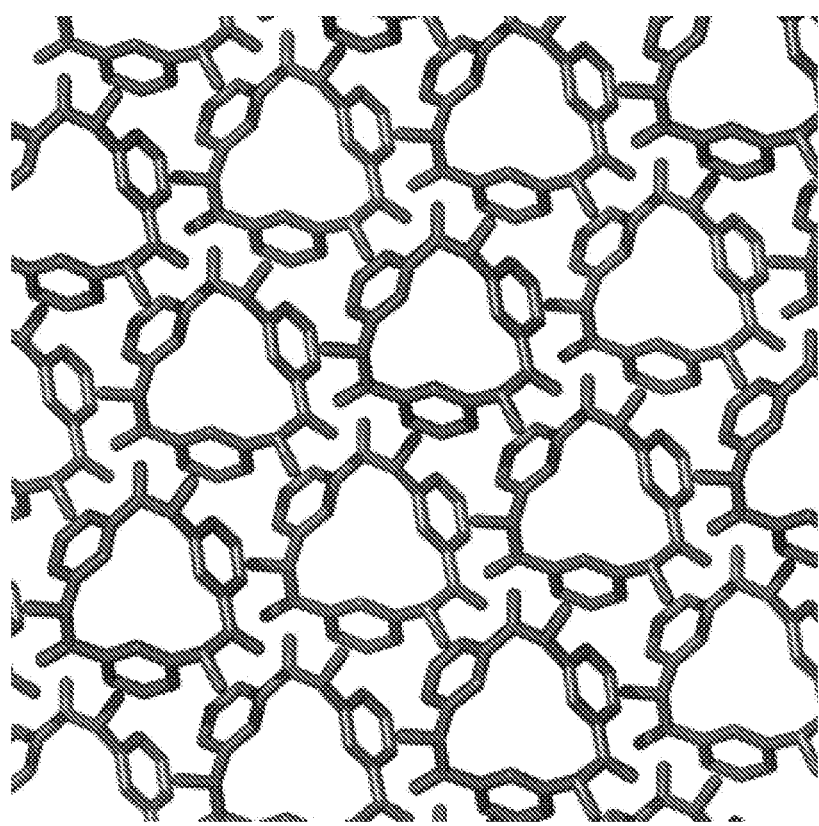
FIG. 3: shows a segment of a crystal packing diagram of (2), viewed along the crystallographic c axis in accordance with an embodiment herein described.

In another embodiment, a crystal-packing diagram of (2) is shown in FIG. 3. Within the a-b crystallographic plane molecules of (2) orient parallel to each other, wherein along the c axis, they similarly stack in a parallel orientation. Each molecule of (2) establishes twelve short [C—H . . . O] contacts (H . . . O distances between 2.50 and 2.60 Å) with twelve of its neighbors. On each benzene ring of (2), the hydrogen positioned ortho relative to the carbonyl group establishes a short contact with a carbonyl oxygen from a neighboring molecule. Similarly, the hydrogen positioned meta to the carbonyl group has contact with the hydroxyl oxygen atoms from three neighboring molecules. As this relationship is reciprocal, C=O and O—H groups from the "other side" of (2) establish short contacts with C—H groups from six additional molecules of (2).

Example 2

Figure 4:
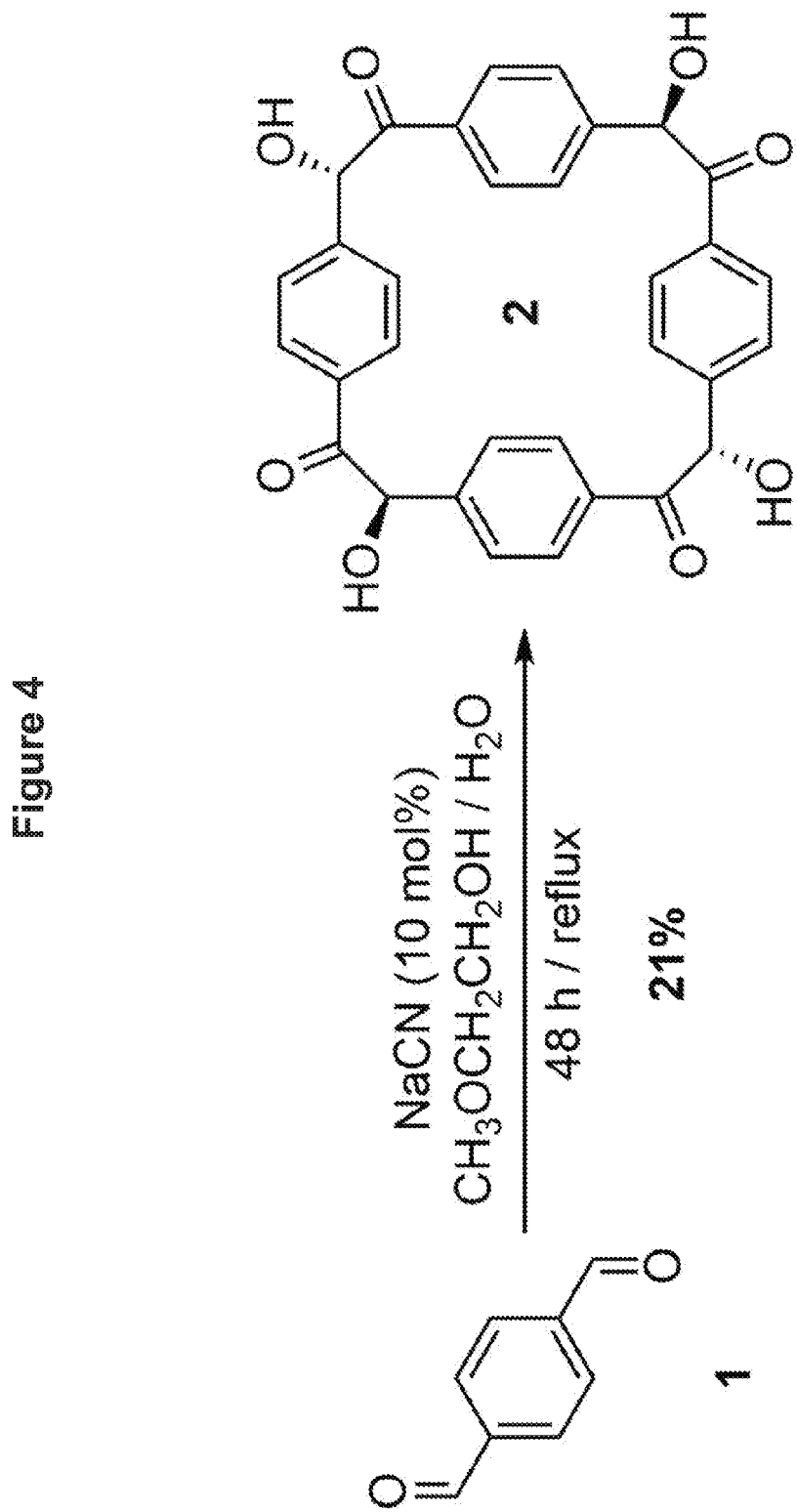
FIG. 4: shows a scheme which depicts the synthesis of cyclotetrabenzoin (2'), in accordance with an embodiment of a method described herein.

Synthesis of Cyclotetrabenzoin ((2'), FIG. 4)

Figure 5:
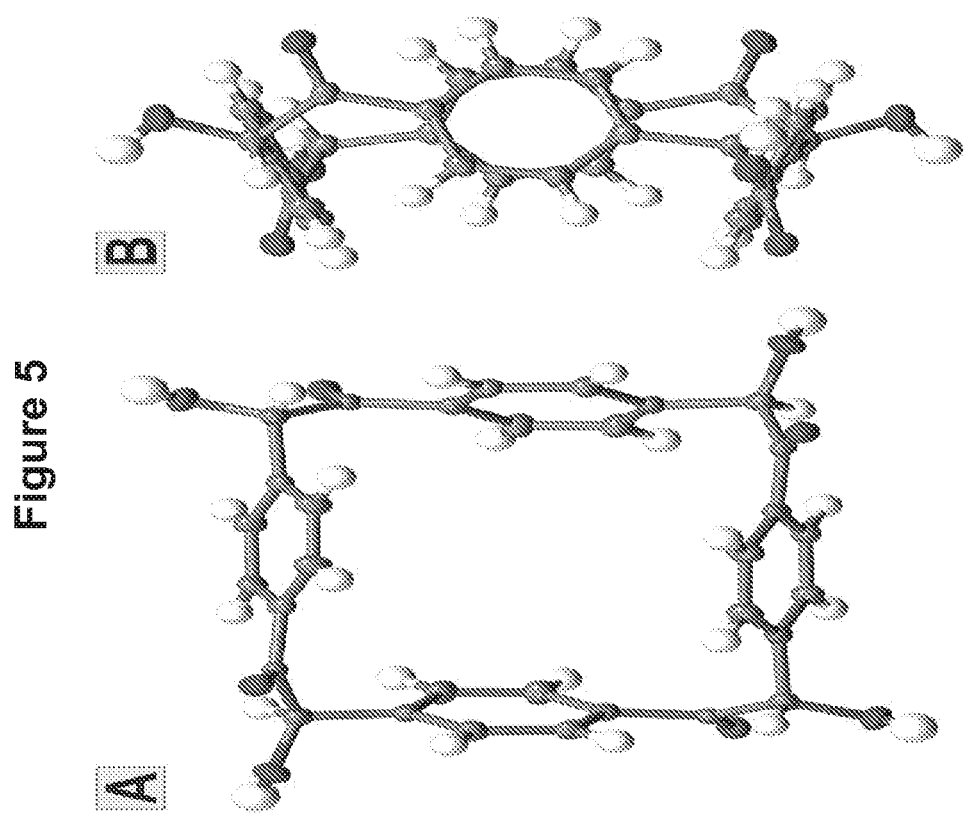
FIG. 5A: shows an X-ray crystal structure of cyclotetrabenzoin (2'), that is a top-down view of the tetramer, showing all α-hydroxyketone functional groups pointing away from the macrocycle cavity in accordance with an embodiment of a method described herein.
FIG. 5B: shows an X-ray crystal structure of cyclotetrabenzoin (2') that is a side view showing the twisted orientation of the benzene rings on the opposite sides of the square tetramer. Thermal ellipsoids shown at 50% probability in accordance with an embodiment of a method described herein.
Figure 6:
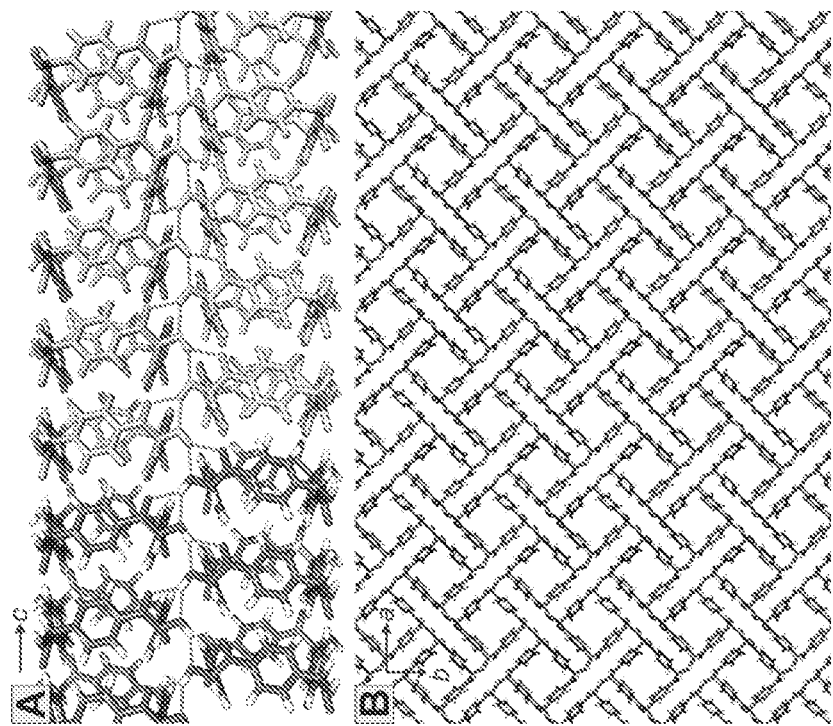

Exposure of 1 to NaCN in a 1:1 mixture of 2-methoxyethanol and $H_2O$, and at a concentration of 1 to 0.167 M, resulted in the formation of a precipitate consisting of the tetramer cyclotetrabenzoin (2'). Recrystallization from DMSO/MeOH produced pure (2') in 21% yield. Single crystals of (2') suitable for X-ray diffraction analysis were grown by slow vapor diffusion of MeOH into a dilute DMSO solution of 2'. Compound 2' crystalizes in the tetragonal space group P421c with two molecules in the unit cell. The four stereocenters of (2') have R, S, R, S configurations, wherein the molecule is achiral, even though it lacks symmetry planes on account of the existence of an S4 axis that passes through the central cavity. In some embodiments, the molecule adopts a roughly square shape (FIG. 5A), with four benzene rings acting as the sides of the square. A central cavity has dimensions of 6.9×6.9 Å, defined as the distances between the centroids of two pairs of benzene rings on the opposite sides of the cyclotetrabenzoin molecule. Some twisting is observable in the planes of the benzene rings (FIG. 5B), as they define a 40.8° angle with the benzene ring on the opposite side. From this perspective, it is also visible that the four α-hydroxyketone functionalities point away from the central cavity, a feature that plays a role in inducing the crystal packing of 2' (FIG. 6). Cyclotetrabenzoin (2') is not strained, as all carbon atoms in (2') have bonding angles within ±2° of their idealized geometries.

X-Ray Crystalography

In some embodiments, the crystal-packing diagram of (2') may be shown as in FIG. 6. In the solid state, the key intermolecular interaction is a bifurcating hydrogen bond established between the benzoin O—H hydrogen and oxygens from both the carbonyl (C=O; O . . . H distance 2.11 Å), and hydroxyl groups (O—H; O . . . H distance 2.16 Å) in the neighboring molecule of 2'. Each macrocycle acts as both a hydrogen bond donor and acceptor, resulting in an infinite "tape" of hydrogen bonds along the crystallographic c axis (as displayed in (A). This relationship is repeated four times on all four sides of the macrocycle. When viewed along the crystallographic c axis, this arrangement results in an ordered square grid (B), wherein individual molecules of 2' are stacked on top of each other, resulting in square-shaped nanotubes. These nanotubes are then bundled through hydrogen bonds established between edge benzoin functionalities, wherein the strong [O—H . . . O] hydrogen bonds are established between molecules from adjacent nanotubes.

In further embodiments, molecules within each individual nanotube engage in comparatively weaker [C—H . . . O] interactions between the benzoin carbonyl group (C=O) oxygen atoms and hydrogen atoms from the aromatic ring as well as the α-protons of benzoin functionality (with H . . . O distances between 2.40 and 3.00 Å). Single crystal X-ray diffraction also determined that no solvent molecules were present in the cavity. The extended structure of (2') wherein FIG. 6 is an example of an intrinsically organic porous molecule, organized into a crystal structure with a 10% void volume (see FIG. 6B). In some embodiments, (2') assembly comprises a highly polar outside groups and nonpolar internal cavities may transport molecular species through crystals and membranes; and its infinitely hydrogen-bonded nanotubular subunits may play a role in the development of novel ferroelectric materials; and finally, it is aesthetically pleasing.

Figure 7:
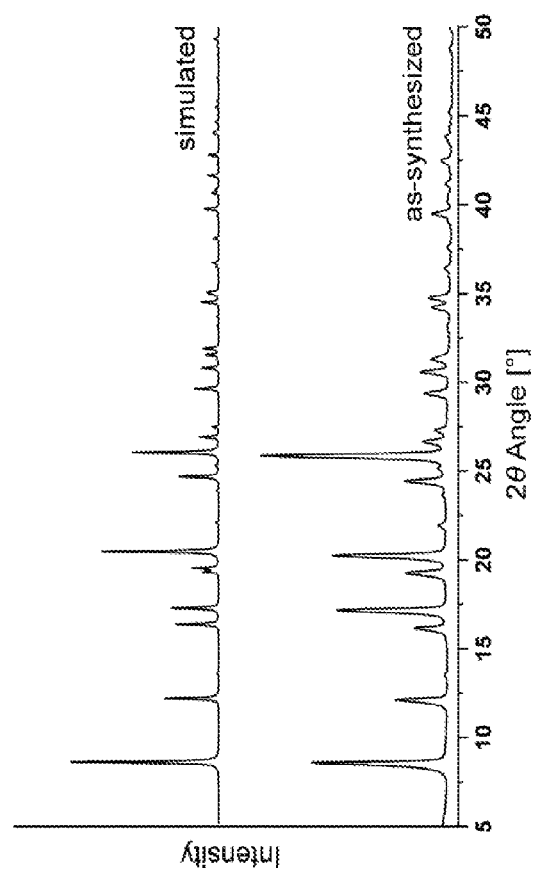
FIG. 7: shows a comparison of PXRD patterns of compound (2'): simulated from single-crystal X-ray data (top) and measured from a freshly recrystallized sample of (2') (bottom), in accordance with an embodiment of a method described herein.
Figure 8:
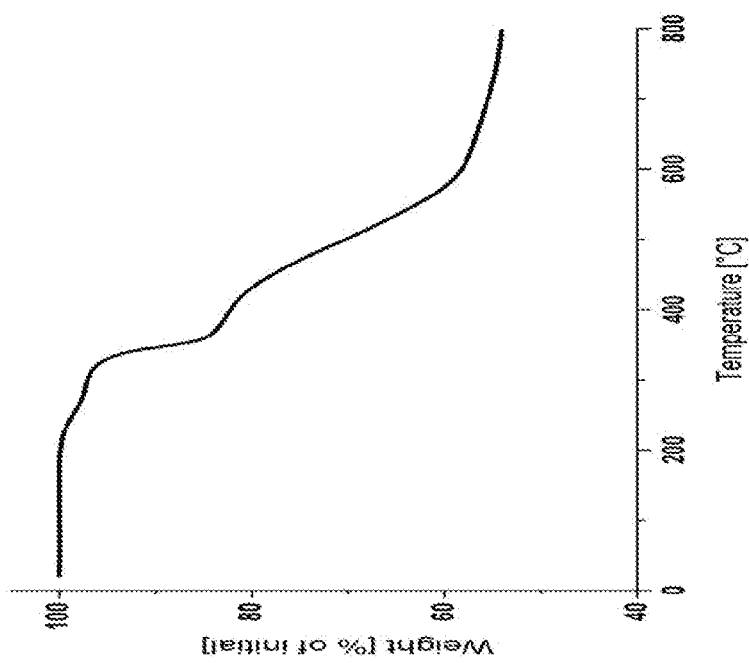
FIG. 8: shows thermogravimetric analysis of compound (2') in accordance with an embodiment of a method described herein.
Figure 9:
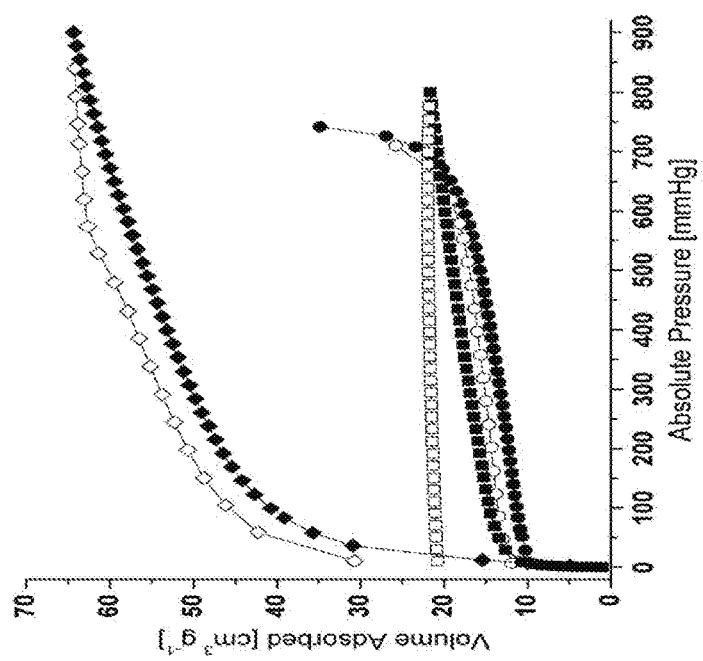
FIG. 9: shows: adsorption (●) and desorption (○) of $N_2$ gas within the pores of (2') measured at 77 K, in accordance with an embodiment of a method described herein.

Macrocycle (2') is microcrystalline after recrystallization; the powder X-ray diffraction (PXRD) pattern of the as synthesized (2') (FIG. 7, bottom) is in agreement with the PXRD pattern simulated from the single crystal X-ray data (FIG. 7, top). The thermal stability of compound (2') was evaluated using thermogravimetric analysis (TGA) under $N_2$, with a heating rate of 2° C. $\min^{-1}$. The TGA trace (FIG. 8) shows no weight loss until about 250° C. Between 250 and 320° C., a small (<4%) weight loss is observed; this is followed by a rapid loss of approx. 14% of the original weight in the 320-360° C. range, and a relatively featureless TGA trace above 360° C., likely indicative of full decomposition. As it is synthesized under aqueous conditions, cyclotetrabenzoin is stable to water. Gas sorption of (2') was probed using $N_2$ as the guest (degassing conditions: 160° C., 15 h, under 10 μmHg). Based on the isotherm (FIG. 9), the Brunauer-Emmett-Teller (BET) and Langmuir surface areas of (2') were determined to be 42 and 52 $m^2g^{-1}$, respectively. The isotherm can be categorized as a hybrid between type I isotherm characteristic for microporous systems, and a small contribution from type II isotherm.

Experimental Details of the Synthesis of Cyclotetrabenzoin (2'):

Terephthaldehyde (1, 6.80 g, 50.0 mmol), 2-methoxyethanol (150 mL), and deionized $H_2O$ (150 mL) were added to a 500 mL round bottom flask equipped with a stirring bar, and the mixture was heated at 100° C. under nitrogen until all 1 dissolved. At that point, NaCN (253 mg, 5.00 mmol) was added into the round bottom flask, and the heating at reflux was continued for 48 h. The precipitate was subjected to a hot filtration and then washed with deionized $H_2O$ (200 mL), MeOH (200 mL), and $Et_2O$ (200 mL). After drying in vacuo, yellowish crude product (2.70 g, 40%) was obtained. This crude material was suspended in DMSO (400 mL) under nitrogen, and heated to 50° C. for 12 h. The resulting yellowish solution was filtered and transferred to a 1 L round bottom flask. Boiling MeOH (500 mL) was then carefully layered on top of the DMSO solution, and the entire mixture was left to cool to 20° C. The round bottom flask was sealed with a septum and filled with $N_2$. A precipitate was obtained; it was filtered and washed with MeOH (100 mL) and $Et_2O$ (100 mL), to give pure (2') as an off-white solid (1.40 g, 21%, mp 299-300° C., with decomposition). $^1H$ NMR (DMSO-$d_6$, 600 MHz): δ=7.83 (d, J=8.4 Hz, 2H), 7.34 (d, J=8.4 Hz, 2H), 6.22 (d, J=5.4 Hz, 2H), 5.91 ppm (d, J=4.8 Hz, 2H) ppm. $^{13}C$ NMR (DMSO-$d_6$, 125 MHz): δ=197.40, 144.59, 132.95, 129.44, 127.12, 76.36 ppm; UV/Vis (DMSO): $\lambda_{max}$ (log ε)=261 (4.68), 318 (3.28) nm; FTIR (KBr pellet): $\tilde{v}$=3456 (s, br), 3057 (w), 2937 (w), 1930 (w), 1807 (w), 1679 (s), 1606 (s), 1413 (m), 1255 (s), 1188 (m), 1122 (m), 1095 (s), 1018 (w), 981 (s), 841 (s), 818 (s), 744 (s), 704 (s) $cm^{-1}$. CI-HRMS: m/z calcd for $C_{32}H_{24}O_8$: 536.1471; found [M+H]+: 537.1548.

In some embodiments, single crystals of (2') were grown as follows. Crude (2') (40 mg) was dissolved in DMSO (20 mL) under heating. The resulting solution was cooled to 20° C. and filtered. Different volumes of the filtrate (0.1-0.5 mL) were added to five small vials (0.8 mL). These vials were then placed inside a larger scintillation vial (20 mL) containing MeOH (4 mL) as the diffusing solvent. The vial was closed and kept at 20° C. for 14 d. Colorless needle-shaped crystals were obtained from all vials. X-ray diffraction data was collected at ChemMatCARS beamline at Advanced Photon Source in Argonne National Laboratory, wherein a colorless needle-shaped crystal measuring 0.10×0.01×0.01 mm³ was mounted on a glass fiber, and cooled to 100 K using Cryojet (Oxford instrumentation). The diffraction data was collected on a Bruker D8 diffractometer with an APEX-II CCD detector using phi scans. Crystal-to-detector distance was 110 mm and the exposure time was 0.3 s per frame using a scan width of 0.5°. Diffraction wavelength was 0.40651 nm. Data collection was 98.2% complete to 14.117° in θ. A total of 24222 reflections were collected, covering the indices: $-21 \leq h \leq 21$, $-21 \leq k \leq 21$ and $-8 \leq l \leq 8$. A total of 2018 reflections were found to be symmetry independent, with an $R_{int}$ of 0.1760. Crystal data of 2: Tetragonal P4 $2_{1c}$, a=b=14.507(3), c=5.8300(10) Å, V=1226.9(5) Å³, Z=2, $\rho_{calcd}$=1.452 Mg/m³, crystal size 0.10×0.01×0.01 mm³, T=100(2) K, μ=0.046 mm-1, R1[I>2σ(I)]=0.0562, wR₂=0.1162, GOF=1.051. Supplementary crystallographic data for this paper have been deposited with the Cambridge Crystallographic Data Centre, under deposition code CCDC 1060952.

In conclusion, disclosed herein is a one-step synthesis of novel highly oxygenated, and shape-persistent macrocycles such as but not limited to cyclotribenzoin (2) and cyclotetrabenzoin (2'). Method of synthesis disclosed herein start with commercially available materials, and are easily scalable. In some embodiments, convergent positioning of aromatic rings on one, and multiple C—H functionalities on the other side of the macrocyclic systems may allow the macrocycles disclosed herein to be utilized as synthetic receptors for cation, anions, or both by virtue of further derivatization of these macrocycle cores, as well as its larger congeners. Similarly, cyclotetrabenzoin (2') may also be a progenitor for an entire class of easily synthesized, shape-persistent, intrinsically porous all-organic macrocycles, where its extensively oxygenated rim allows the molecule to engage in strong hydrogen bonds, which in one embodiment, plays a role in its assembly in the solid state, and in another embodiment may be utilized to bind discrete molecular guests. While its surface area is small, its chemical and thermal stability are superior to the previously reported intrinsically porous organic cages of the prior art, and in further embodiments, an isoreticular series of analogs of (2') may further be synthesized by switching the central p-phenylene motif of terephthaldehyde for longer biphenylene- or triphenylene-based precursors.

While exemplary embodiments of the invention have been shown and described, modifications thereof can be made by one skilled in the art without departing from the spirit and teachings of those embodiments. The embodiments described herein are exemplary only, and are not intended to be limiting. Many variations and modifications of the disclosed embodiments are possible and are within the scope of the claimed invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, RI, and an upper limit, Ru, is disclosed, any number falling within the range is specifically disclosed. In particular, the following numbers within the range are specifically disclosed: R=RI+k* (Ru-RI), wherein k is a variable ranging from 1 percent to 100 percent with a 1 percent increment, i.e., k is 1 percent, 2 percent, 3 percent, 4 percent, 5 percent, . . . 50 percent, 51 percent, 52 percent, . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the above-identified embodiments of the present invention. The disclosures of all patents, patent applications, and publications cited herein are hereby incorporated by reference, to the extent that they provide exemplary, procedural or other details supplementary to those set forth herein.

What is claimed is:

1. A one-step method of synthesizing a cyclobenzoin macrocycle, comprising:

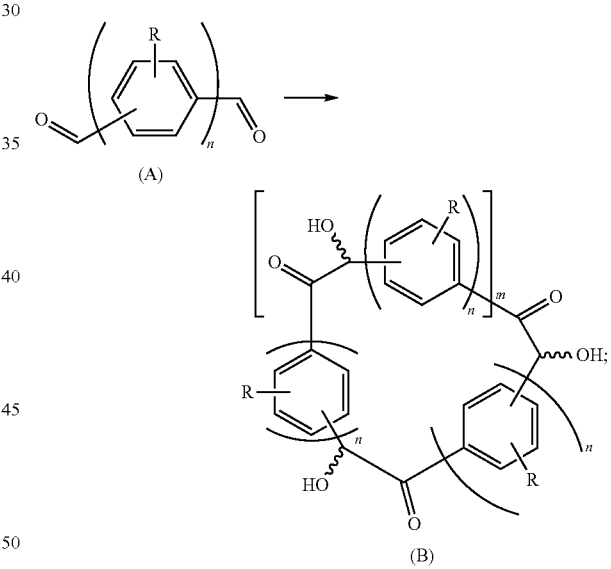

reacting a dialdehyde (A) in a concentration of between 0.1M to 1M, and a cyanide salt catalyst in an aqueous solvent wherein said solvent is in a 1:1 molar ratio with $H_2O$ to form a cyclobenzoin (B) macrocycle, wherein n is selected from group comprising 1, 2, or 3; and M is 3, or 4, and wherein said reacting the dialdehyde and the cyanide salt catalyst comprises refluxing at a temperature of about 100° C.

2. The method of claim 1, wherein said solvent is an alcohol.

3. The method of claim 2, wherein said alcohol is selected from the group consisting of 2-methoxyethanol; ethanol; methanol; propanol, butanol, pentanol isomers, and glycols.

4. The method of claim 1, wherein said dialdehyde is selected from the group consisting of isophthaldehyde;

tetraphthaldehyde; phthaldehyde, and aromatic analogs thereof, wherein one or more substituted or unsubstituted aromatic or hetoroaromatic rings, and/or triple bonds are inserted between two formyl groups.

5. The method of claim 4, wherein said dialdehyde is isophthaldehyde in a concentration of about 0.5M.

6. The method of claim 4, wherein said dialdehyde is tetraphthaldehyde in a concentration of about 0.17M.

7. The method of claim 1, wherein said reacting a dialdehyde and a cyanide salt comprises refluxing under nitrogen gas at a temperature of about 100° C. for about 48 hrs.

8. The method of claim 1, wherein said cyanide salt is selected from the group consisting of NaCN, cyanide salts of metals; and thiazolium salts.

9. The method of claim 5, wherein said cyclobenzoin macrocycle is cyclotribenzoin or a cyclotetrabenzoin.

10. The method of claim 1, wherein said cyclobenzoin macrocycle forms a microporous three-dimensional organic framework, or a one dimensional nanotube channel.

11. The method of claim 1, wherein said cyclobenzoin macrocycle is porous.

12. The method of claim 1, wherein said cyclotetrabenzoin comprises a Langmuir surface area of about 52 $m^2g^{-1}$.

13. The method of claim 1, wherein said cyclobenzoin macrocycles further comprise porous materials, assemblies at liquid-solid interfaces, or organic nanowires and nanofibrils.

14. The method of claim 1, wherein said cyclobenzoin comprises a synthetic receptor macromolecule.

15. A cyclotetrabenzoin macrocycle; comprising:
   a square shape-persistent 3-dimensional structure, wherein said square shape-persistent 3-dimensional structure comprises four outer polar α-hydroxyketone moieties; and
   a central nonpolar cavity, or a cone shape-persistent 3-dimensional structure, wherein said cone shape-persistent 3-dimensional structure comprises convergent anionic and cationic binding groups .

16. The cyclotetrabenzoin macrocycle of claim 15, wherein said macrocycle is intrinsically porous, and comprises a 10% void volume.

17. The cyclotetrabenzoin macrocycle of claim 15, wherein said central non-polar cavity comprises an area of about 6.9×6.9Å.

18. The cyclotetrabenzoin macrocycle of claim 15, wherein said α-hydroxyketone moieties comprise hydrogen bonds to further units of cyclotetrabenzoin to form hydrogen-bonded nanotubular subunits.

19. The cyclotetrabenzoin macrocycle of claim 15, wherein said α-hydroxyketone moieties comprise hydrogen bonds to molecular guest molecules.

20. The cyclotetrabenzoin macrocycle of claim 15, wherein said α-hydroxyketone moieties, cationic binding groups, or anioic binding groups are selectively derivatized.

21. The cyclotribenzoin macrocycle of claim 20, wherein said anionic and cationic binding groups bond with guest molecules.

* * * * *